(12) United States Patent
Makita et al.

(10) Patent No.: US 12,274,586 B2
(45) Date of Patent: Apr. 15, 2025

(54) TEST DEVICE, TEST SYSTEM, ULTRASONIC DIAGNOSTIC DEVICE, ACOUSTIC COUPLING MATERIAL DEVICE, AND STORAGE MEDIUM

(71) Applicant: CANON MEDICAL SYSTEMS CORPORATION, Otawara (JP)

(72) Inventors: Yasuhisa Makita, Nasushiobara (JP); Yoichi Ogasawara, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 573 days.

(21) Appl. No.: 17/469,146

(22) Filed: Sep. 8, 2021

(65) Prior Publication Data

US 2022/0079566 A1 Mar. 17, 2022

(30) Foreign Application Priority Data

Sep. 11, 2020 (JP) .................................. 2020-153057

(51) Int. Cl.
*A61B 8/00* (2006.01)
*G16H 40/40* (2018.01)

(52) U.S. Cl.
CPC .............. *A61B 8/58* (2013.01); *A61B 8/4281* (2013.01); *A61B 8/4438* (2013.01); *G16H 40/40* (2018.01)

(58) Field of Classification Search
CPC ........ A61B 8/58; A61B 8/4281; A61B 8/4438
See application file for complete search history.

(56) References Cited

U.S. PATENT DOCUMENTS

| 5,517,994 A * | 5/1996 | Burke ................... G01S 7/5205 600/443 |
| 2007/0220980 A1* | 9/2007 | Tanaka .................. G01S 7/5205 73/649 |
| 2011/0040187 A1* | 2/2011 | Matsumura .......... A61B 5/6843 600/443 |
| 2011/0251489 A1* | 10/2011 | Zhang .................. A61B 8/4227 600/459 |
| 2014/0241115 A1 | 8/2014 | Thattari Kandiyil et al. |
| 2017/0290567 A1* | 10/2017 | Fujita ..................... A61B 8/488 |

(Continued)

FOREIGN PATENT DOCUMENTS

| JP | H0576528 A | * | 3/1993 |
| JP | 7-178083 A | | 7/1995 |

OTHER PUBLICATIONS

Combined Chinese Office Action and Search Repot issued on Jun. 29, 2023 in Chinese Patent Application No. 202111048368.1 (with English translation of Category of Cited Documents), 8 pages.

*Primary Examiner* — Angela M Hoffa
*Assistant Examiner* — Younhee Choi
(74) *Attorney, Agent, or Firm* — Oblon, McClelland, Maier & Neustadt, L.L.P.

(57) ABSTRACT

A test device of an embodiment includes processing circuitry. The processing circuitry is configured to detect a waveform of a reflected wave that is obtained by reflection of an ultrasonic wave, which has been transmitted from an ultrasonic probe and has passed through an acoustic coupling material in close contact with an acoustic radiation surface of the ultrasonic probe, the reflected wave having passed through the acoustic coupling material before the detection of the waveform, and test a performance of the ultrasonic probe on the basis of the detected waveform.

6 Claims, 7 Drawing Sheets

(56) References Cited

U.S. PATENT DOCUMENTS

| | | | |
|---|---|---|---|
| 2018/0153517 A1* | 6/2018 | Chang | A61N 7/00 |
| 2019/0269943 A1* | 9/2019 | Lewis, Jr. | G10K 11/02 |
| 2020/0253589 A1* | 8/2020 | Cao | A61B 8/145 |

* cited by examiner

SIGNAL WAVEFORM

SIGNAL WAVEFORM

TEST DEVICE, TEST SYSTEM, ULTRASONIC DIAGNOSTIC DEVICE, ACOUSTIC COUPLING MATERIAL DEVICE, AND STORAGE MEDIUM

CROSS-REFERENCE TO RELATED APPLICATION

The present application claims priority based on Japanese Patent Application No. 2020-153057 filed Sep. 11, 2020, the content of which is incorporated herein by reference.

FIELD

Embodiments disclosed in the present description and drawings relate to a test device, a test system, an ultrasonic diagnostic device, an acoustic coupling material device, and a storage medium.

BACKGROUND

A plurality of vibrators are arranged in an acoustic radiator of an ultrasonic probe. When an ultrasonic probe is used for a long time, for example, characteristics thereof change with time due to deterioration of the vibrators and influence of usage environment. Accordingly, the performance of an ultrasonic probe is checked by regularly testing it to confirm that no abnormalities have occurred in the ultrasonic probe.

Conventionally, for example, an ultrasonic probe is fixed with an inspection jig, a reflector is installed in a direction in which the ultrasonic probe transmits ultrasonic waves through a solvent such as water, and waveforms of reflected waves of ultrasonic waves caused to be transmitted from the ultrasonic probe toward the reflector, and the like are used to check the performance of the ultrasonic probe. However, in this method, it is difficult to perform alignment when the ultrasonic probe is fixed with the jig and to stably perform a test. Alternatively, there is also a technique of testing the performance of an ultrasonic probe using reflected waves obtained by reflection of ultrasonic waves, which has been transmitted from the ultrasonic probe, on a lens surface. However, in this technique, the noise included in reflected waves is large and it is difficult to test the performance.

DETAILED DESCRIPTION

Hereinafter, a test device, a test system, an ultrasonic diagnostic device, an acoustic coupling material device, and a storage medium of embodiments will be described with reference to the drawings.

A test device of an embodiment includes processing circuitry. The processing circuitry is configured to detect a waveform of a reflected wave that is obtained by reflection of an ultrasonic wave, which has been transmitted from an ultrasonic probe and has passed through an acoustic coupling material in close contact with an acoustic radiation surface of the ultrasonic probe, the reflected wave having passed through the acoustic coupling material before the detection of the waveform, and test a performance of the ultrasonic probe on the basis of the detected waveform.

First Embodiment

Figure 1:
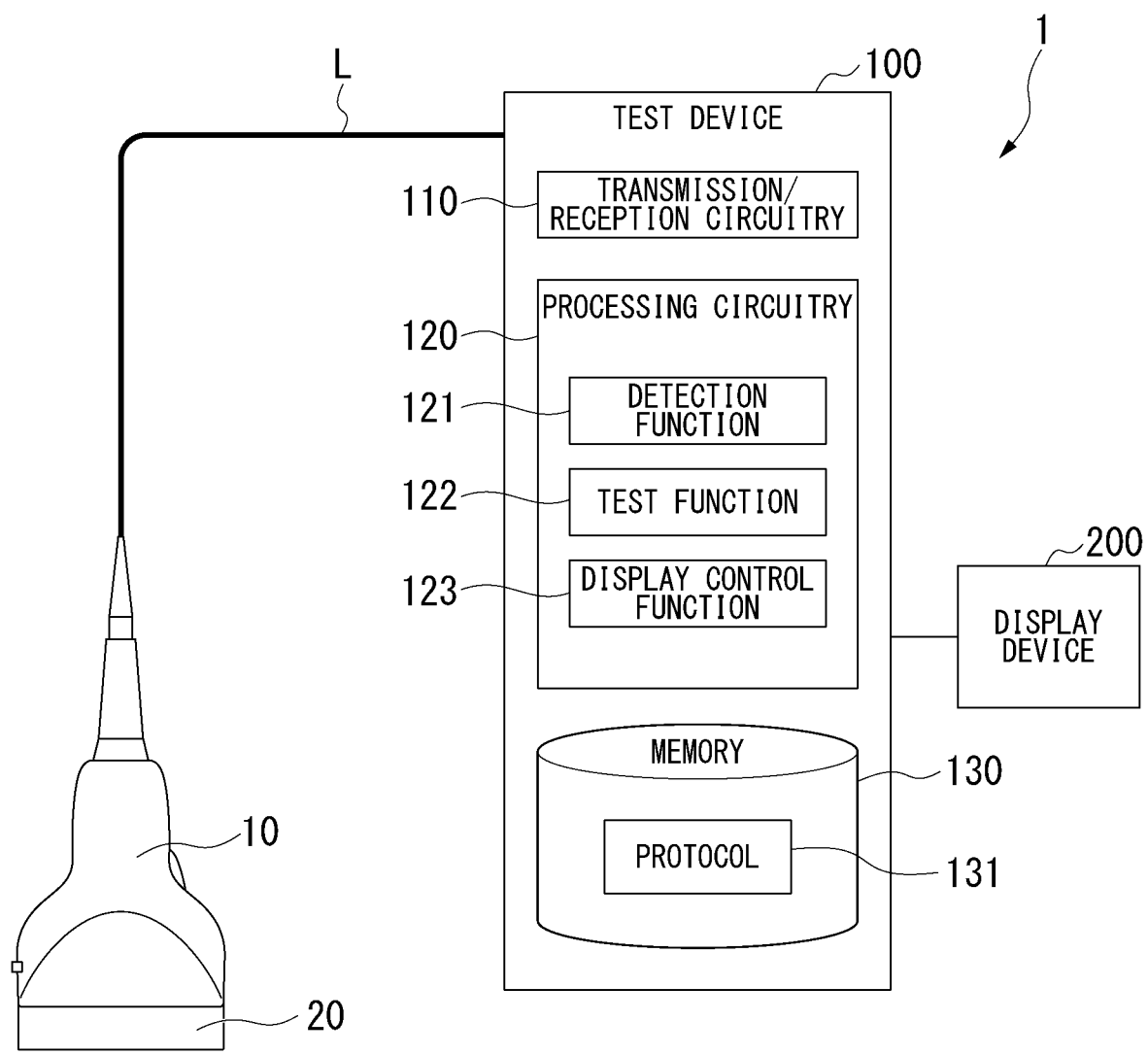
FIG. 1 is a diagram showing an example of a configuration of a test system 1 according to a first embodiment.

FIG. 1 is a diagram showing an example of a configuration of a test system 1 according to a first embodiment. For example, the test system 1 tests the performance of an ultrasonic probe by testing detection accuracy and the like when reflected waves of ultrasonic waves transmitted from an ultrasonic probe 10 are received and waveforms of the reflected waves are detected. The test system 1 includes, for example, an acoustic coupling material 20, a test device 100, and a display device 200.

The ultrasonic probe 10 is used, for example, to perform ultrasonic diagnosis on a subject. The test device 100 is used to test the performance of the ultrasonic probe 10 when ultrasonic diagnosis is not performed in the ultrasonic probe 10. At the time of performing ultrasonic diagnosis on a subject, for example, the ultrasonic probe 10 transmits ultrasonic waves to the subject in order to acquire an image of the inside of the subject on the basis of a driving signal output from an ultrasonic diagnostic device 300 (refer to FIG. 9). The ultrasonic probe 10 receives reflected waves of the transmitted ultrasonic waves through an acoustic radiation surface 16. The ultrasonic probe 10 generates reflected wave information based on the received reflected waves of the ultrasonic waves and transmits the reflected wave information to the ultrasonic diagnostic device 300.

For example, the ultrasonic probe 10 transmits ultrasonic waves in response to a driving signal output from the test device 100 when it is provided to test the performance thereof. The ultrasonic probe 10 receives reflected waves of the transmitted ultrasonic waves through the acoustic radiation surface 16. The ultrasonic probe 10 generates reflected wave information based on the received reflected waves of the received ultrasonic waves and transmits the reflected wave information to the test device 100.

Figure 2:
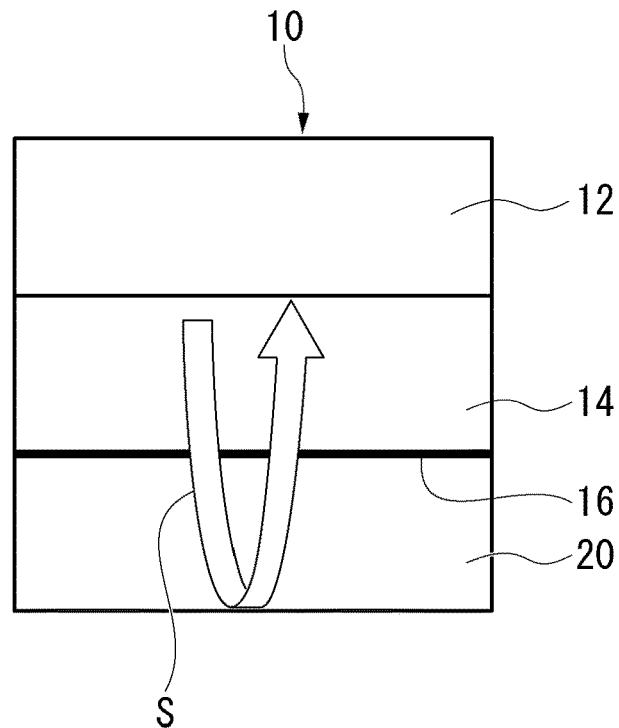
FIG. 2 is an enlarged cross-sectional view of a part of an ultrasonic probe 10 according to the first embodiment.

FIG. 2 is an enlarged cross-sectional view of a part of the ultrasonic probe 10 according to the first embodiment. The ultrasonic probe 10 includes, for example, a vibrator 12 and a lens 14. The vibrator 12 includes a plurality of vibrating elements, and each vibrating element vibrates in response to a driving signal output from the test device 100 to transmit ultrasonic waves. The ultrasonic waves transmitted by the vibrator 12 pass through the lens 14. The lens 14 adjusts focuses of the ultrasonic waves that pass therethrough. The ultrasonic waves that have passed through the lens 14 are transmitted to the outside through the acoustic radiation surface 16. The acoustic radiation surface 16 is, for example, a surface opposite to a surface of the lens 14 in contact with the vibrator 12.

The acoustic coupling material 20 is a material suitable to test the ultrasonic probe 10, for example, rubber, and is in an approximately rectangular parallelepiped shape, for example. The acoustic coupling material 20 is bonded to the acoustic radiation surface 16 of the ultrasonic probe 10 using an acoustic coupling agent (a jellied acoustic coupling agent) such as SONO Jelly (registered trademark), an adhesive, or the like and attached to the acoustic radiation surface 16 in a state in which it is in close contact with the acoustic radiation surface 16 at the time of testing the performance of the ultrasonic probe 10. The acoustic coupling material 20 may be a material other than rubber and may be, for example, a member obtained by encapsulating a gelled or liquid acoustic coupling agent in a bag.

The distance (the thickness of the acoustic coupling material 20) between a contact surface of the acoustic coupling material 20 which is in close contact with the acoustic radiation surface 16 of the ultrasonic probe 10 and an opposite surface opposite to the contact surface is adjusted to a distance suitable to test the ultrasonic probe 10. The ultrasonic waves transmitted from the ultrasonic probe 10 pass through the acoustic coupling material 20 and are reflected by the opposite surface of the acoustic coupling material 20 to become reflected waves. The opposite surface of the acoustic coupling material 20 is an interface opposite to a surface of the acoustic coupling material 20 which is in close contact with the lens 14. The acoustic coupling material 20 is in close contact with the ultrasonic probe 10, and thus both ultrasonic waves transmitted from the ultrasonic probe 10 and reflected waves obtained by reflection of the ultrasonic waves pass through the acoustic coupling material 20.

The test device 100 includes, for example, transmission/reception circuitry 110, processing circuitry 120, and a memory 130. The transmission/reception circuitry 110 includes, for example, driving circuitry for driving the vibrator 12 of the ultrasonic probe 10, and the like. The transmission/reception circuitry 110 outputs a driving signal to the ultrasonic probe 10 through a cable L according to transmission/reception conditions transmitted from the processing circuitry 120. The transmission/reception circuitry 110 acquires reflected wave information output from the ultrasonic probe 10. The transmission/reception circuitry 110 converts the acquired reflected wave information into a digital signal.

The processing circuitry 120 has, for example, a detection function 121, a test function 122, and a display control function 123. The processing circuitry 120 realizes these functions, for example, by a hardware processor executing a program stored in the memory (storage circuit) 130. The hardware processor means, for example, circuitry such as a central processing unit (CPU), a graphics processing unit (GPU), an application specific integrated circuit (ASIC), a programmable logic device (e.g., a simple programmable logic device (SPLD) or a complex programmable logic device (CPLD)), or a field programmable gate array (FPGA) (the same applies in the following). The program may be directly incorporated in the circuit of the hardware processor instead of being stored in the memory 130. In this case, the hardware processor realizes functions by reading and executing the program incorporated in the circuit. The hardware processor is not limited to a configuration of a single circuit and may be configured as a single hardware processor by combining a plurality of independent circuits to realize respective functions. In addition, the respective functions may be realized by a single hardware processor in which a plurality of components are integrated.

The memory 130 is realized, for example, by a semiconductor memory element such as a random access memory (RAM) or a flash memory, a hard disk, an optical disc, or the like. The memory 130 stores a protocol 131 when the performance of the ultrasonic probe 10 is tested. The protocol 131 is a procedure when the performance of the ultrasonic probe 10 is tested and, for example, differs depending on types of the ultrasonic probe 10 and the acoustic coupling material 20 attached to the ultrasonic probe 10. Such data may be stored in an external memory with which the test device 100 can communicate instead of the memory 130 (or in addition to the memory 130). The external memory is controlled, for example, by a cloud server that manages the external memory by receiving a read/write request.

The detection function 121 detects waveforms of reflected waves that are obtained by reflection of ultrasonic waves, which have been transmitted from the ultrasonic probe 10 and passed through the acoustic coupling material 20 in close contact with the acoustic radiation surface 16 of the ultrasonic probe 10, and have passed through the acoustic coupling material 20. Accordingly, the detection function 121 detects waveforms of reflected waves received by the ultrasonic probe 10 on the basis of reflected wave information transmitted from the ultrasonic probe 10. The detection function 121 is an example of a detector.

The test function 122 causes the transmission/reception circuitry 110 to output a driving signal to the ultrasonic probe 10 such that the ultrasonic probe 10 transmits ultrasonic waves with a predetermined waveform according to the protocol 131 stored in the memory 130. The test function 122 detects signal waveforms including the waveform of the ultrasonic waves caused to be transmitted by the ultrasonic probe 10 and the waveform of reflected waves output from the detection function 121 and tests the performance of the ultrasonic probe 10 on the basis of the detected signal waveforms.

The display control function 123 causes the display device 200 to display an image. The display control function 123 causes the display device 200 to display, for example, an image of signal waveforms transmitted from the ultrasonic probe 10. The display device 200 is, for example, a liquid crystal display. The display device 200 may be a device that displays images and may be, for example, a projector.

Figure 3:
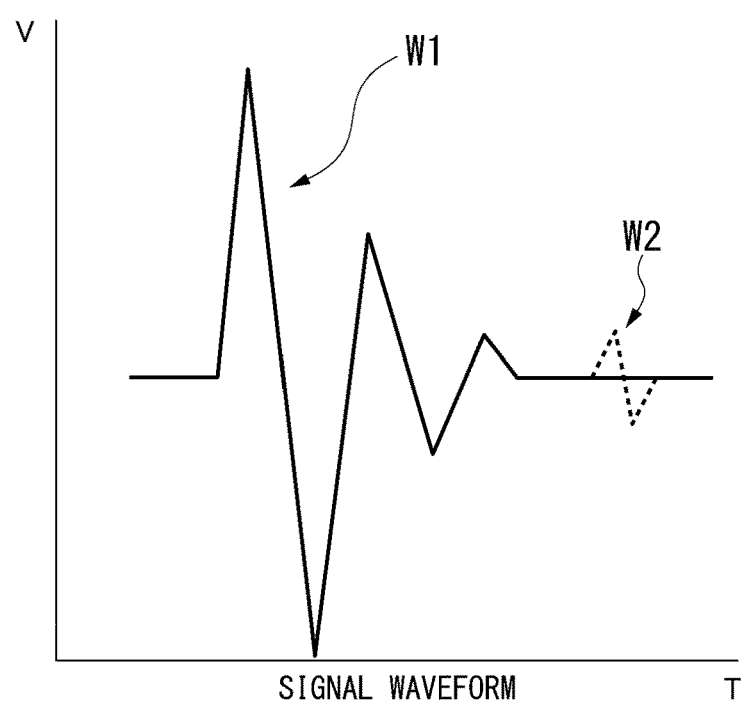
FIG. 3 is a diagram showing temporal change in signal waveforms detected by a test device 100 according to the first embodiment.

FIG. 3 is a diagram showing temporal change in signal waveforms detected by the test device 100 according to the first embodiment. The test function 122 extracts a received waveform W2 from signal waveforms including an initial waveform W1 and the received waveform W2 detected by the detection function 121, for example. The test function 122 tests the performance of the ultrasonic probe 10 on the basis of the extracted signal waveforms.

The test function 122 tests the performance of the ultrasonic probe 10, for example, on the basis of the amplitude and time of flight (TOF) of the received waveform W2. The test function 122 determines that the performance of the ultrasonic probe 10 has deteriorated when the amplitude of the received waveform W2 is less than a predetermined value as a test result. The predetermined value used for the test is determined, for example, depending on a driving signal output to the ultrasonic probe 10. The test function 122 is an example of a tester.

The test device 100 of the first embodiment causes the ultrasonic probe 10 to transmit ultrasonic waves and to receive reflected waves of the ultrasonic waves to test the performance of the ultrasonic probe 10. At this time, the acoustic coupling material 20 is in close contact with the ultrasonic probe 10. As shown in FIG. 2, ultrasonic waves transmitted from the vibrator 12 of the ultrasonic probe 10 and reflected waves (hereinafter "transmitted/received waves") S thereof pass through the acoustic coupling material 20 in addition to the lens 14. Accordingly, a path through which the transmitted/received waves S pass lengthens according to the acoustic coupling material 20 being provided as compared to a case in which the acoustic coupling material 20 is not provided.

Figure 4:
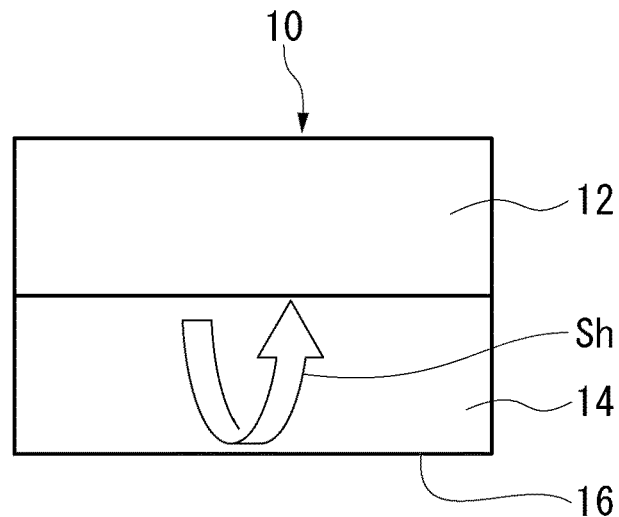
FIG. 4 is an enlarged cross-sectional view of a part of the ultrasonic probe 10 in which an acoustic coupling material 20 is not provided according to the first embodiment.
Figure 5:
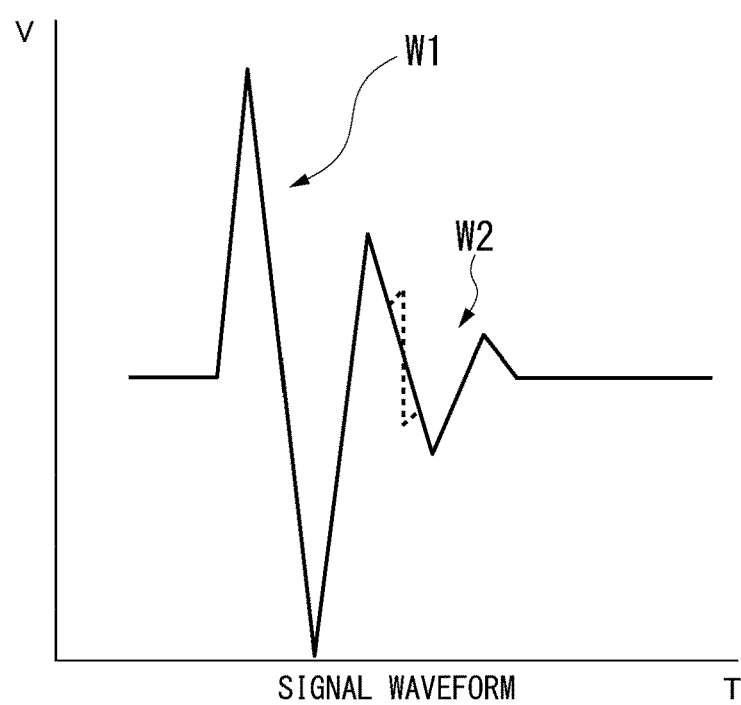
FIG. 5 is a diagram showing temporal change in signal waveforms detected by the test device 100 when the acoustic coupling material 20 is not provided in the ultrasonic probe 10 according to the first embodiment.

On the other hand, for example, a case in which the acoustic coupling material 20 is not provided in the ultrasonic probe 10 is assumed. FIG. 4 is an enlarged cross-sectional view of a part of the ultrasonic probe 10 in which the acoustic coupling material 20 is not provided according to the first embodiment and FIG. 5 is a diagram showing temporal change in signal waveforms detected by the test device 100 when the acoustic coupling material 20 is not provided in the ultrasonic probe 10 according to the first embodiment.

When the acoustic coupling material 20 is not provided, for example, ultrasonic waves transmitted from the vibrator 12 are reflected by the acoustic radiation surface 16 of the lens 14 to become reflected waves, and the vibrator 12 receives these reflected waves. In this case, the distance in which transmitted/received waves Sh pass shortens. Accordingly, the interval between a time at which an initial waveform W1 appears and a time at which a received waveform W2 appears decreases and thus resolution for the initial waveform W1 and the received waveform W2 decreases.

On the other hand, when the acoustic coupling material 20 is provided in the ultrasonic probe 10 and thus the path through which the transmitted/received waves S pass lengthens, the time from when the ultrasonic probe 10 transmits ultrasonic waves to when the ultrasonic probe 10 receives reflected waves increases accordingly. Consequently, the time difference between a time at which the initial waveform W1 appears and a time at which the received waveform W2 appears can be increased in signal waveforms detected by the test function 122, and thus the initial waveform W1 and the received waveform W2 can be satisfactorily separated from each other. As a result, noise included in the received waves can be reduced and thus the performance of the ultrasonic probe can be tested with high accuracy.

In the first embodiment, the acoustic coupling material 20 is in close contact with the ultrasonic probe, for example, using an adhesive. Accordingly, it is not necessary to use a jig for supporting the ultrasonic probe 10, a solvent such as water, and the like. Therefore, it is possible to test the performance of the ultrasonic probe 10 through a simple device.

Second Embodiment

Figure 6:
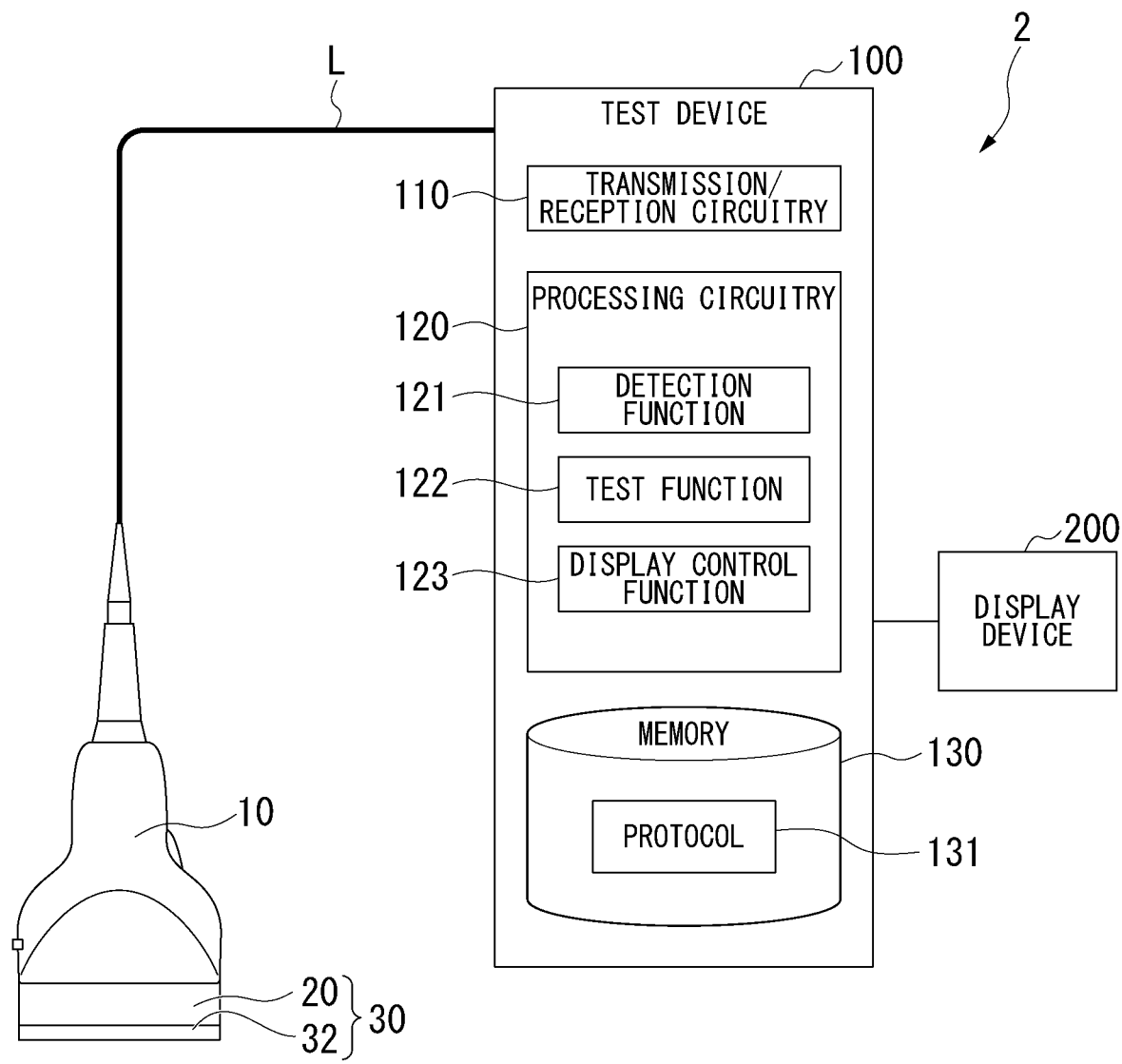
FIG. 6 is a diagram showing an example of a configuration of a test system 2 according to a second embodiment.

FIG. 6 is a diagram showing an example of a configuration of a test system 2 of a second embodiment. The test system 2 of the second embodiment differs from the first embodiment in that it includes an acoustic coupling material device 30. The acoustic coupling material device 30 includes the same acoustic coupling material 20 as that of the first embodiment and a reflector 32 in close contact with the acoustic coupling material 20.

The acoustic coupling material 20 is attached to the ultrasonic probe 10 in close contact therewith as in the first embodiment. The reflector 32 is attached in close contact with an opposite surface of the acoustic coupling material 20, which is opposite to the contact surface in close contact with the ultrasonic probe 10. The reflector 32 reflects ultrasonic waves transmitted from the ultrasonic probe 10 to generate reflected waves to be used to test the performance of the ultrasonic probe. The reflector 32 is a rigid body made of, for example, a metal. The reflector 32 may be made of a material other than a metal and may be made of, for example, a resin.

The test system 2 of the second embodiment includes the acoustic coupling material device 30. The acoustic coupling material 20 in the acoustic coupling material device 30 is attached to the ultrasonic probe 10 in close contact therewith as in the test system 1 of the first embodiment. Accordingly, a path through which the transmitted/received waves S pass lengthens and a time difference between a time at which the initial waveform W1 appears and a time at which the received waveform W2 appears when test is performed in the test device 100 can be increased, and thus the S/N ratio can be improved. Further, it is not necessary to use a jig for supporting the ultrasonic probe 10, a solvent such as water, and the like. Therefore, it is possible to test the performance of the ultrasonic probe 10 through a simple device.

Since the reflector 32 in the test system 2 of the second embodiment is a rigid body, a relative positional relation with respect to the ultrasonic probe 10 can be stabilized. Accordingly, it is easy to maintain a constant distance between the lens 14 and the reflector 32, in other words, the distance in which the transmitted/received waves S pass. Therefore, a stable test becomes possible and, for example, detailed data such as TOF can also be tested with high accuracy.

Third Embodiment

Figure 7:
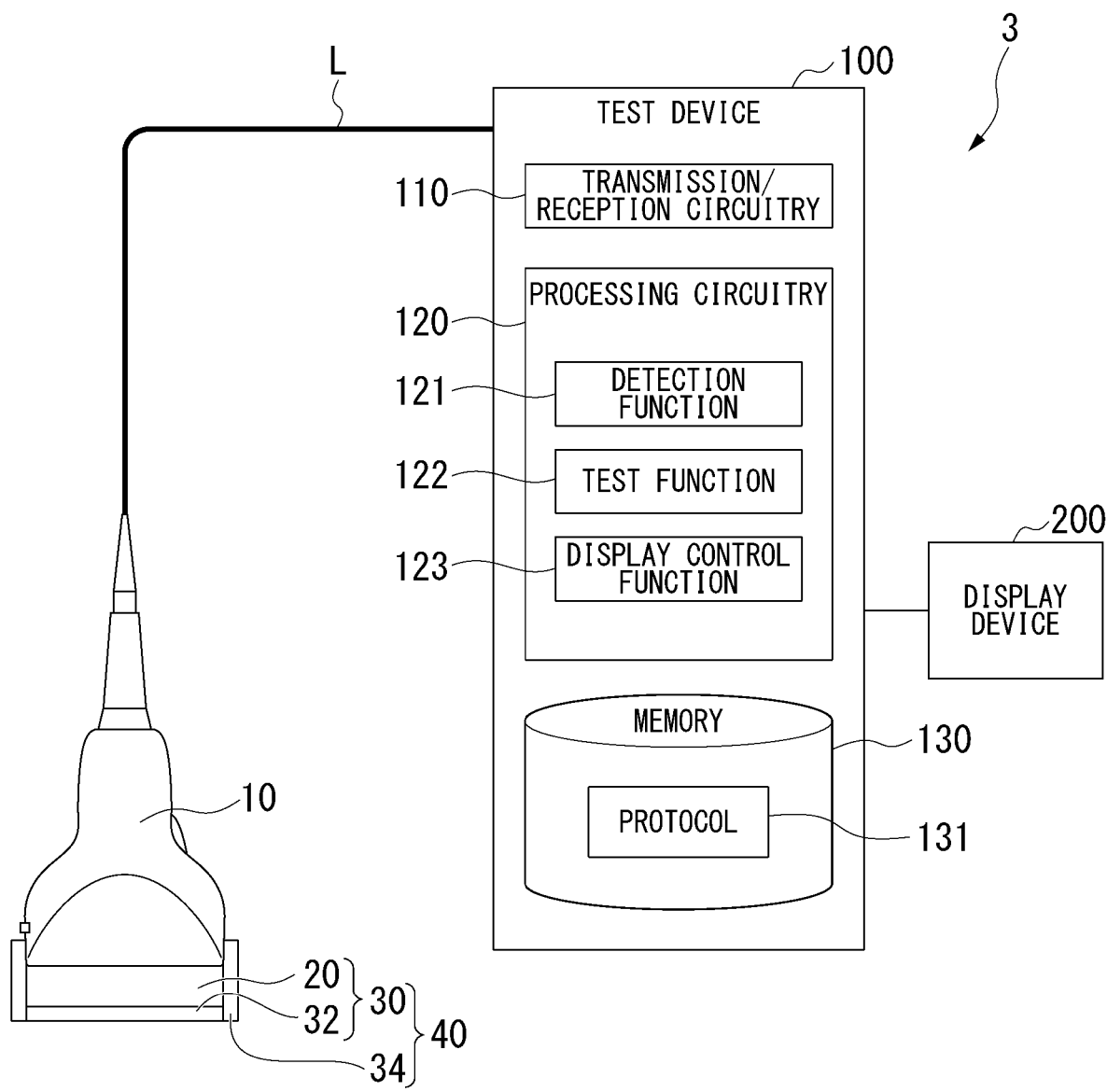
FIG. 7 is a diagram showing an example of a configuration of a test system 3 according to a third embodiment.

FIG. 7 is a diagram showing an example of a configuration of a test system 3 of a third embodiment. The test system 3 of the third embodiment differs from the first embodiment in that it includes an acoustic coupling material unit 40. The acoustic coupling material unit 40 includes the same acoustic coupling material device 30 as that of the second embodiment and a supporting member 34 that causes the reflector 32 in the acoustic coupling material device 30 to be supported by the ultrasonic probe 10.

The reflector 32 is fixed to the supporting member 34. The supporting member 34 includes a fitter fitted in a case for accommodating the vibrator 12 in the ultrasonic probe 10. The shape of the inside of the fitter is approximately consistent with the outer shape of the case for accommodating the vibrator 12 in the ultrasonic probe 10. For example, the supporting member 34 is caused to slide from the side of the acoustic radiation surface 16 in the ultrasonic probe 10 such that the supporting member 34 is fitted in the case of the ultrasonic probe 10. By fitting the supporting member 34 in the case of the ultrasonic probe 10, the reflector 32 is supported by the ultrasonic probe 10.

The test system 3 of the third embodiment includes the acoustic coupling material device 30. Accordingly, it is possible to test the performance of the ultrasonic probe with high accuracy by reducing noise included in received waves and to test the performance of the ultrasonic probe 10 through a simple device. Further, in the test system 3 of the third embodiment, the reflector 32 is supported by the case of the ultrasonic probe 10 through the supporting member 34. Accordingly, it is possible to easily set the reflector 32 and securely support the reflector 32.

The supporting member 34 in the acoustic coupling material device 30 may be implemented in a different aspect. For example, one or both of the case of the ultrasonic probe 10 and the supporting member 34 may include a magnet and the other that is not a magnet may be a metal or the like such that the case of the ultrasonic probe 10 can support the reflector 32 via a magnetic force. Alternatively, fitters fitted to each other may be set in both the case of the ultrasonic probe 10 and the supporting member 34 and these fitters may be fitted to each other such that the case of the ultrasonic probe 10 can support the reflector 32.

Fourth Embodiment

Figure 8:
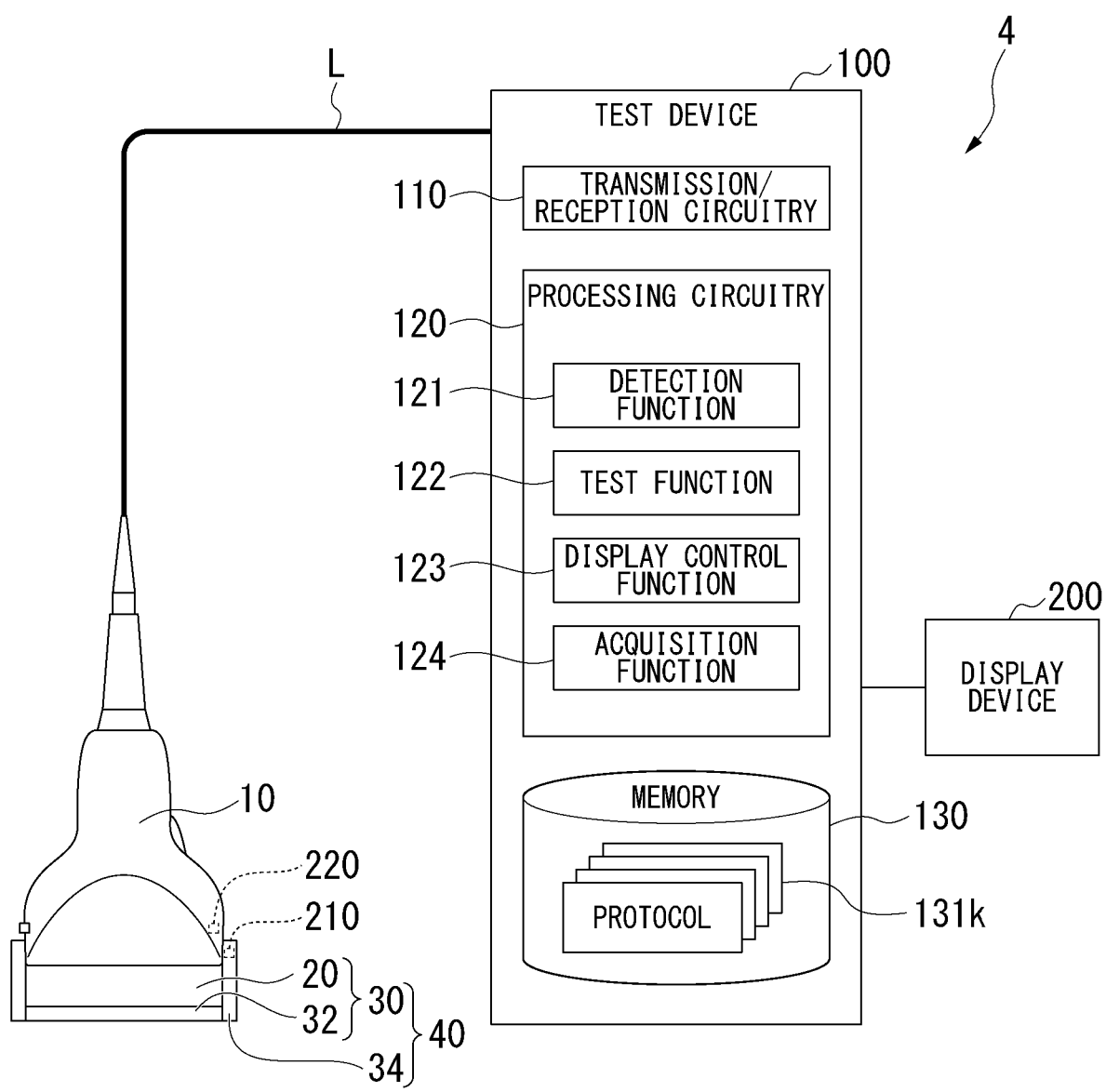
FIG. 8 is a diagram showing an example of a configuration of a test system 4 according to a fourth embodiment.

FIG. 8 is a diagram showing an example of a configuration of a test system 4 of a fourth embodiment. The test system 4 of the fourth embodiment differs from the third embodiment in that an IC tag 210 is provided in the acoustic coupling material unit 40 and an IC tag reader 220 is provided in the ultrasonic probe 10. Further, the test system 4 of the fourth embodiment differs from the third embodiment in that an acquisition function 124 is further provided in the processing circuitry 120 of the test device 100 and a plurality of k-th protocols 131$k$ (k=1, 2, 3, n, the same applies in the following) are stored in the memory 130. When orders of protocols are not distinguished, sign "k" is omitted and protocols are represented as a protocol 131.

The IC tag 210 stores, for example, identification information that identifies an acoustic coupling material. The identification information includes, for example, information that identifies the acoustic coupling material 20 to which the IC tag 210 is attached, for example, an acoustic coupling material number. The IC tag reader 220 transmits a read signal to the IC tag 210 and reads the identification information stored in the IC tag 210. The acoustic coupling material number is determined, for example, when the acoustic coupling material is manufactured. The ultrasonic probe 10 transmits and provides the identification information read by the IC tag reader 220 to the test device 100. The IC tag 210 is an example of a storage.

The transmission/reception circuitry 110 of the test device 100 receives the identification information transmitted from the ultrasonic probe 10 and outputs the identification information to the acquisition function 124. The acquisition function 124 acquires the acoustic coupling material number indicated by the identification information transmitted from the ultrasonic probe 10. The test function 122 selects a single k-th protocol 131$k$ of the plurality of protocols 131 stored in the memory 130 on the basis of the acoustic coupling material number acquired by the acquisition function 124. The selected k-th protocol 131$k$ includes a test procedure depending on a thickness and a material of a region through which ultrasonic waves pass in the acoustic coupling material 20 in close contact with the acoustic radiation surface 16 of the ultrasonic probe 10.

The test function 122 causes the transmission/reception circuitry 110 to output a driving signal to the ultrasonic probe 10 such that the ultrasonic probe 10 transmits ultrasonic waves with a predetermined waveform according to the selected k-th protocol 131$k$. The acquisition function 124 is an example of an acquirer, and the protocol 131 is an example of test information.

For each acoustic coupling material number, a k-th protocol 131$k$ stored in the memory 130 includes information on a protocol for testing the ultrasonic probe 10 to which the corresponding acoustic coupling material is attached. A protocol for testing the ultrasonic probe 10 to which the corresponding acoustic coupling material is attached is determined in advance depending on characteristics (e.g., the thickness and the material of the region through which ultrasonic waves pass) of the acoustic coupling material and stored in the memory 130.

The test system 4 of the fourth embodiment includes the acoustic coupling material device 30. Accordingly, the performance of the ultrasonic probe can be tested with high accuracy by reducing noise included in received waves and the performance of the ultrasonic probe 10 can be tested through a simple device. Further, in the test system 4 of the fourth embodiment, the IC tag reader 220 provided in the ultrasonic probe 10 reads the acoustic coupling material information that is stored in the IC tag 210 and identifies the acoustic coupling material 20, and the test device 100 tests the performance of the ultrasonic probe 10 through a protocol depending on characteristics of the acoustic coupling material 20. Accordingly, the ultrasonic probe 10 can be tested through a protocol depending on the acoustic coupling material 20 attached to the ultrasonic probe 10, and thus testing with high accuracy can be performed.

Furthermore, the IC tag reader 220 reads the acoustic coupling material information stored in the IC tag 210. Accordingly, even when an operator who tests the performance of the ultrasonic probe 10 mistakes the acoustic coupling material 20 attached to the ultrasonic probe 10, for example, the operator can correctly perform testing.

Fifth Embodiment

Figure 9:
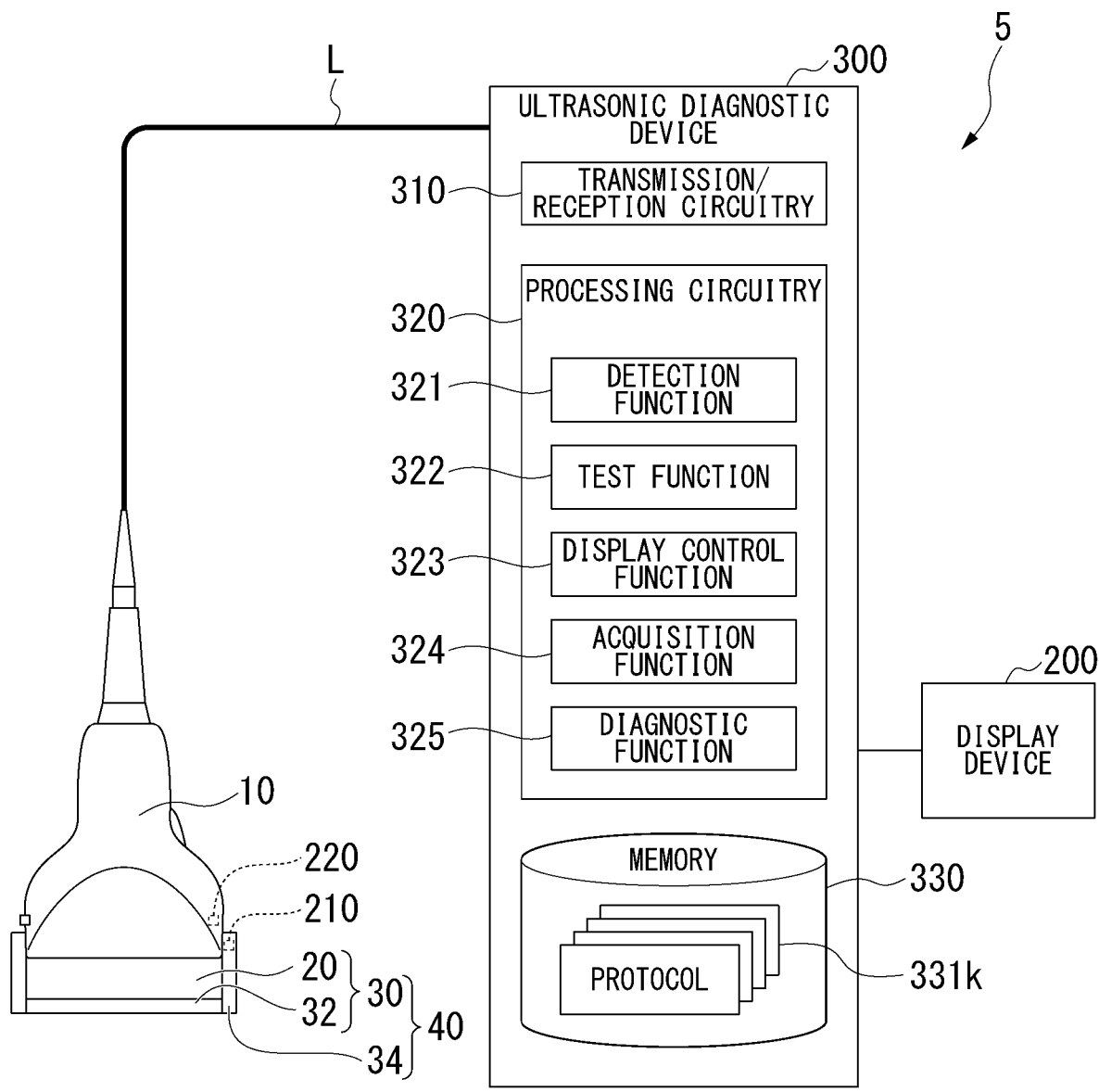
FIG. 9 is a diagram showing an example of a configuration of an ultrasonic diagnostic system 5 according to a fifth embodiment.

FIG. 9 is a diagram showing an example of a configuration of an ultrasonic diagnostic system 5 of a fifth embodiment. The ultrasonic diagnostic system 5 of the fifth embodiment includes the ultrasonic diagnostic device 300 instead of the test device 100 of each of the above-described embodiments. The ultrasonic diagnostic device 300 executes testing of the performance of the ultrasonic probe 10 and ultrasonic diagnosis using the ultrasonic probe 10. The ultrasonic diagnostic device 300 executes the same processing as that of the test device 100 described in the first to fourth embodiments at the time of testing the performance of the ultrasonic probe 10. In ultrasonic diagnosis using the ultrasonic probe 10, the ultrasonic diagnostic device 300 causes the ultrasonic probe 10 to transmit ultrasonic waves toward a subject such that the ultrasonic waves are reflected from the subject. The ultrasonic probe 10 receives the reflected waves of the ultrasonic waves, generates reflected wave information, and transmits the reflected wave information to the ultrasonic diagnostic device 300. The ultrasonic diagnostic device 300 acquires information on the subject to be used for diagnosis on the basis of the transmitted reflected wave information.

The ultrasonic diagnostic device 300 includes, for example, transmission/reception circuitry 310, processing circuitry 320, and a memory 330. The transmission/reception circuitry 310 has the same configuration as that of the transmission/reception circuitry 110 of the first embodiment. The processing circuitry 320 has, for example, a detection function 321, a test function 322, a display control function 323, an acquisition function 324, and a diagnostic function 325. The processing circuitry 320 realizes these functions, for example, by a hardware processor executing a program stored in the memory 330. The program may be directly incorporated in the circuit of the hardware processor instead of being stored in the memory 330, or a plurality of components may be integrated into a single hardware processor to realize respective functions. The memory 330 stores a plurality of k-th protocols 331k when the performance of the ultrasonic probe 10 is tested like the memory 130 of the fourth embodiment.

The detection function 321, the test function 322, the display control function 323, and the acquisition function 324 have the same functions as the detection function 121, the test function 122, the display control function 123, and the acquisition function 124 of the fourth embodiment. The detection function 321 outputs detected waveforms of reflected waves to the test function 322 and the diagnostic function 325. The diagnostic function 325 mainly functions, for example, at the time of ultrasonic diagnosis using the ultrasonic probe 10, whereas the test function 322 mainly functions at the time of testing the performance of the ultrasonic probe 10.

When ultrasonic diagnosis is performed, the diagnostic function 325 outputs transmission/reception conditions to the transmission/reception circuitry 310 and controls a transmission voltage output from the transmission/reception circuitry 310 to the ultrasonic probe 10. The diagnostic function 325 acquires information on the subject used for ultrasonic diagnosis on the basis of waveforms of reflected waves obtained by reflecting the ultrasonic waves transmitted from the ultrasonic probe 10 by the subject. The reflected waves are output to the diagnostic function 325 through the detection function 321. The diagnostic function 325 generates information to be provided to a tester or a doctor on the basis of the acquired information on the subject and provides the information. The diagnostic function 325 is an example of a diagnoser.

The ultrasonic diagnostic system 5 of the fifth embodiment includes the acoustic coupling material device 30. Accordingly, the performance of the ultrasonic probe can be tested with high accuracy by reducing noise included in received waves and the performance of the ultrasonic probe 10 can be tested through a simple device. Further, in the ultrasonic diagnostic system 5 of the fifth embodiment, the IC tag reader 220 provided in the ultrasonic probe 10 reads the acoustic coupling material information that is stored in the IC tag 210 and identifies the acoustic coupling material 20 and the ultrasonic diagnostic device 300 tests the performance of the ultrasonic probe 10 through a protocol depending on characteristics of the acoustic coupling material 20. Accordingly, the ultrasonic probe 10 can be tested through a protocol depending on the acoustic coupling material 20 attached to the ultrasonic probe 10, and thus testing with high accuracy can be performed.

Further, in the ultrasonic diagnostic system 5 of the fifth embodiment, the ultrasonic diagnostic device includes the same test function 322 as the test function 122 included in the test device 100 of the fourth embodiment. Accordingly, in diagnosis of the performance of the ultrasonic probe 10 used for ultrasonic diagnosis using the ultrasonic diagnostic device, the effort of disconnecting the ultrasonic probe 10 from the ultrasonic diagnostic device and re-connecting it to a measurement device can be saved. Therefore, even when a tester, a doctor, or the like who performs ultrasonic diagnosis becomes an operator who tests the performance of the ultrasonic probe 10, for example, they can test the performance of the ultrasonic probe 10 without requiring much efforts. Although the performance of the ultrasonic probe 10 that can be tested using the test device 100 is only a specific type in each embodiment, a plurality of types of ultrasonic probes 10 can also be tested using the test device 100. In this case, the test device 100 may store protocols depending on the plurality of ultrasonic probes 10 and may test the performance of an ultrasonic probe 10 through a protocol depending on probe identification information that identify the ultrasonic probe, which is provided by the ultrasonic probe 10.

Although the IC tag reader 220 is provided in the ultrasonic probe 10 in the test system 4 of the fourth embodiment and the ultrasonic diagnostic system 5 of the fifth embodiment, the IC tag reader 220 may be provided in a device other than the ultrasonic probe 10. The IC tag reader 220 may be provided, for example, in the test device 100 or the ultrasonic diagnostic device 300. In this case, when the ultrasonic probe 10 is tested, the IC tag 210 provided in the acoustic coupling material 20 may be brought close to the IC tag reader 220 provided in the test device 100 or the ultrasonic diagnostic device 300 and the IC tag reader 220 may be caused to read the acoustic coupling material information stored in the IC tag 210.

According to at least one embodiment described above, it is possible to test the performance of an ultrasonic probe with high accuracy through a simple device by including a detector which detects a waveform of a reflected wave that is obtained by reflection of an ultrasonic wave, which has been transmitted from the ultrasonic probe and has passed through an acoustic coupling material in close contact with an acoustic radiation surface of the ultrasonic probe, the reflected wave having passed through the acoustic coupling material before the detection of the waveform, and a tester which tests performance of the ultrasonic probe on the basis of the waveform detected by the detector.

Although several embodiments have been described, these embodiments have been suggested as examples and are not intended to limit the scope of the invention. These embodiments can be implemented in other various forms and various omissions, substitutions and modifications are possible without departing from essential characteristics of the invention. These embodiments and modifications thereof are included in the scope and essential characteristics of the invention and also included in the invention disclosed in claims and the equivalents thereof.

What is claimed is:

1. A test system, comprising:
    a test device;
    an ultrasonic probe; and
    an acoustic coupling material unit comprising an acoustic coupling material in close contact with an acoustic radiation surface of the ultrasonic probe, wherein the test device comprises:
    processing circuitry configured to:
        detect a waveform of a reflected wave that is obtained by reflection of an ultrasonic wave, which has been transmitted from the ultrasonic probe and has passed through the acoustic coupling material, the reflected wave having passed through the acoustic coupling material before the detection of the waveform; and
        test a performance of a plurality of vibrators of the ultrasonic probe based on the detected waveform; and
    a memory storing a plurality of test procedures each including a corresponding waveform of a corresponding ultrasonic wave to be transmitted from the ultrasonic probe, the plurality of test procedures being determined in advance depending on a thickness and a material of a region of a corresponding acoustic coupling material through which the ultrasonic wave passes wherein:
    an Integrated Circuit (IC) tag is provided in the acoustic coupling material unit, an IC tag reader is provided in the ultrasonic probe, the IC tag stores particular identification information that identifies the acoustic coupling material, the IC tag reader reads the particular identification information stored in the IC tag, and the ultrasonic probe transmits the particular identification information read by the IC tag reader to the test device, and the processing circuitry is further configured to acquire, from among the plurality of test procedures stored in the memory, a test procedure depending on the particular identification information transmitted from the ultrasonic probe; and test the performance of the plurality of vibrators of the ultrasonic probe based on the waveform of the reflected wave detected by causing the ultrasonic probe to transmit the ultrasonic wave with a particular waveform according to the acquired test procedure.

2. The test system according to claim 1, wherein the processing circuitry is further configured to detect the waveform of the reflected wave reflected by an interface opposite to a surface in close contact with the ultrasonic probe in the acoustic coupling material.

3. The test system according to claim 1, wherein the processing circuitry is further configured to detect the waveform of the reflected wave reflected by a reflector provided on an opposite surface opposite to a surface in close contact with the ultrasonic probe in the acoustic coupling material.

4. The test system according to claim 3, wherein the processing circuitry is further configured to detect the waveform of the reflected wave reflected by the reflector, which is supported by the ultrasonic probe through a supporting member.

5. An ultrasonic diagnostic device, comprising:

the test system according to claim 1; and circuitry configured to cause an ultrasonic wave transmitted from the ultrasonic probe to be reflected from a subject and acquire information on the subject based on the reflected wave reflected from the subject.

6. A non-transitory computer-readable storage medium storing a program causing processing circuitry of a test device to perform a method, wherein the test device is configured to control an ultrasonic probe having an integrated circuit (IC) reader provided therein, the ultrasound probe being connected to an acoustic coupling material unit comprising an acoustic coupling material in close contact with an acoustic radiation surface of the ultrasonic probe, the acoustic coupling material unit including an IC tag storing particular identification information that identifies the acoustic coupling material, the test device including a memory storing a plurality of test procedures each including a corresponding waveform of a corresponding ultrasonic wave to be transmitted from the ultrasonic probe, the plurality of test procedures being determined in advance depending on a thickness and a material of a region of a corresponding acoustic coupling material through which the ultrasonic wave passes, the method comprising:

detecting a waveform of a reflected wave that is obtained by reflection of the ultrasonic wave, which has been transmitted from the ultrasonic probe and has passed through the acoustic coupling material, the reflected wave having passed through the acoustic coupling material before the detection of the waveform; and testing a performance of a plurality of vibrators of the ultrasonic probe based on the detected waveform, wherein the method further comprises:

receiving, from the ultrasound probe, identification information identifying the acoustic coupling material;

acquiring, from among the plurality of test procedures stored in the memory, a test procedure depending on the identification information received from the ultrasonic probe, the identification information having been read from the IC tag by the IC tag reader of the ultrasound probe; and testing the performance of the plurality of vibrators of the ultrasonic probe based on the waveform of the reflected wave detected by causing the ultrasonic probe to transmit the ultrasonic wave with a particular waveform according to the acquired test procedure.

* * * * *